United States Patent [19]
Amano et al.

[11] Patent Number: 4,587,100
[45] Date of Patent: May 6, 1986

[54] MULTILAYER ANALYTICAL ELEMENT FOR THE DETECTION OF HYDROGEN PEROXIDE

[75] Inventors: Yoshikazu Amano; Fuminori Arai; Masao Kitajima, all of Asaka, Japan

[73] Assignee: Fuji Photo Film Co., Ltd., Kanagawa, Japan

[21] Appl. No.: 530,207

[22] Filed: Sep. 8, 1983

[30] Foreign Application Priority Data

Sep. 10, 1982 [JP] Japan ................................ 57-157442

[51] Int. Cl.$^4$ ..................... G01N 21/78; G01N 31/22; C12Q 1/00
[52] U.S. Cl. ....................................... 422/56; 422/60; 435/11; 435/14
[58] Field of Search ...................... 435/11, 14; 422/56, 422/60

[56] References Cited

U.S. PATENT DOCUMENTS 3,983,005  9/1976  Goodhue et al. ...................... 435/11
3,992,158  11/1976  Przybylowicz et al. .............. 422/57
4,292,272  9/1981  Kitajima et al. ....................... 422/56

Primary Examiner—Christine M. Nucker
Attorney, Agent, or Firm—Toren, McGeady, Stanger, Goldberg & Kiel

[57] ABSTRACT

A multilayer analytical element comprising a water-impermeable, light-transmissive support, a reagent layer containing at least a peroxidase, and a porous spreading layer, which are superposed in this order, in which at least one layer other than said support contains a water-soluble monocarboxylic acid or a salt thereof having solubility of not less than 1 g. in 100 g. of water at 25° C.

9 Claims, No Drawings

MULTILAYER ANALYTICAL ELEMENT FOR THE DETECTION OF HYDROGEN PEROXIDE

BACKGROUND OF THE INVENTION

1. Field of the Invention

This invention relates to a multilayer analytical element. More particularly, this invention relates to a multilayer analytical element containing a color indicator system and a peroxidase for detection of hydrogen peroxide which is appropriately employable in quantitative analysis of hydrogen peroxide in a liquid sample, or in quantitative analysis of a specific component through quantitative determination of the amount of hydrogen peroxide produced upon contact of the specific component with an oxidase enzyme system.

2. Description of Prior Arts

A quantitative analysis of a specific component (referred to herein as "analyte") based on quantitative determination of the amount of $H_2O_2$ produced by an oxidation reaction between the analyte or a reaction product of the analyte and an oxidase enzyme, by means of an appropriate determination procedure has recently become more important. The reason is that the quantitative determination of $H_2O_2$ can be done accurately and reliably, for instance, by photometric determination of a colored product formed by the action of $H_2O_2$ in the presence of peroxidase.

As for the photometric determination method based on the above-mentioned principle, there is known a method using a reagent system proposed by P. Trinder (See Ann. Clin. Biochem., 6, 24–27 (1969)). This method involves: producing $H_2O_2$ by a reaction between an analyte and an oxidase; causing an oxidative coupling reaction between 4-aminoantipyrine (or an analogue thereof) and a phenol (or a naphthol) in the presence of $H_2O_2$ and a peroxidase to produce a colored product; and quantitatively determining the so produced colored product. This reaction system is advantageous because the same detection system is employable regardless of varying the kind of oxidase. Accordingly, this reaction system has been studied for application in detection of various analytes. Examples of analytes particularly important in the art of clinical chemical tests include glucose oxidase, cholesterol oxidase, uricase, glycerol oxidase, and phosphoglucose oxidase.

An analytical element employing said oxidase and a detection system for the produced $H_2O_2$ in the form of an integral multilayer analytical element or a strip (such as a filter paper strip) impregnated with these reagents is widely employed for clinical tests. This analytical element comprises a composition containing reagents directly participating in the detection of an analyte which is impregnated in a filter paper strip or the like or coated over a filmy support.

As one example of the multilayer analytical elements containing a color indicator system and a peroxidase, there can be mentioned a multilayer analytical element for quantitative analysis of glucose containing glucose oxidase, peroxidase, 1,7-dihydroxynaphthalene and 4-aminoantipyrine disclosed in U.S. Pat. No. 4,292,272.

The present inventors have studied a multilayer analytical element formulated according to the above-mentioned system and noted that the optical density of color formed in the reagent layer is reduced in the case of using a hemolytic whole blood or hemolytic plasma as a liquid sample, as compared with the case of using a non-hemolytic whole blood or non-hemolytic plasma as the liquid sample. Further noted was that the observed glucose concentration in the former case is lowered than that in the latter case. Upon further studies on this problem, the present inventors have found that this problem is assumed to arise from interference by catalase or substances having a catalase activity contained in the blood.

Accordingly, the present inventors have earnestly continued their studies for elimination of the above-mentioned interference and discovered that the interference by catalase or substances having a catalase activity contained in a blood occurring in a multilayer analytical element for quantitative analysis of glucose is eliminated by incorporating a water-soluble monocarboxylic acid or a salt thereof such as acetic acid or sodium acetate into a constitutional layer such as a layer containing glucose oxidase or a reagent layer containing peroxidase, whereby the color formation efficiency therein is increased and further the reaction rate of a series of the reactions concerned is enhanced. The present invention has been completed upon the discovery.

SUMMARY OF THE INVENTION

A primary object of the present invention is to provide a multilayer analytical element containing a color-forming reagent composition including peroxidase for detection of $H_2O_2$ in a reagent layer, which is substantially free from the interference caused by catalase or substances having a catalase activity (hereinafter, both are simply referred to as "catalase") contained in a blood sample.

Another object of the invention is to provide a multilayer analytical element containing a color-forming reagent composition including oxidase and peroxidase for detection of $H_2O_2$ in a reagent layer, which is substantially free from the interference caused by catalase contained in a blood sample.

A further object of the invention is to provide a multilayer analytical element containing a color-forming reagent composition including oxidase and peroxidase for detection of $H_2O_2$ in a reagent layer, which is so improved as to show a high reaction rate under analytical conditions, whereby enabling reduction of the period required for the quantitative analytical procedure.

A still further object of the invention is to provide a multilayer analytical element containing a color-forming reagent composition including oxidase and peroxidase for detection of $H_2O_2$ in a reagent layer, in which the measurable range is broadened.

The present invention provides a multilayer analytical element comprising a water-impermeable, light-transmissive support, a reagent layer containing at least a peroxidase, and a porous spreading layer, which are superposed in this order, in which at least one layer other than said support contains a water-soluble monocarboxylic acid or a salt thereof having solubility of not less than 1 g. in 100 g. of water at 25° C.

Examples of the preferred embodiments of the present invention include:

(1) The multilayer analytical element, in which said monocarboxylic acid is an aliphatic monocarboxylic acid or an aromatic monocarboxylic acid.

(2) The multilayer analytical element, in which said monocarboxylic acid or salt thereof is at least one compound selected from the group consisting of formic acid, acetic acid, propionic acid, butyric acid, valeric acid, benzoic acid, an alkali metal salt thereof, and an ammonium salt thereof.

(3) The multilayer analytical element as described in the above (2), in which said alkali metal salt is selected from the group consisting of a lithium salt, a potassium salt and a sodium salt.

(4) The multilayer analytical element as described in the above, in which said reagent layer contains 4-aminoantipyrine or a derivative thereof in addition to the peroxidase.

(5) The multilayer analytical element as described in the above, in which an oxidase is contained in said reagent layer or any other layer.

(6) The multilayer analytical element as described in the above (5), in which said oxidase is selected from the group consisting of glycollate oxidase, malate oxidase, glucose oxidase, hexose oxidase, cholesterol oxidase, L-gulonolactone oxidase, galactose oxidase, xanthine oxidase, pyruvate oxidase, uricase, ascorbate oxidase, lactate oxidase, glycine oxidase, and glycerol oxidase.

(7) The multilayer analytical element as described in the above (5), in which said oxidase is glucose oxidase.

(8) The multilayer analytical element as described in the above (5), in which said oxidase is cholesterol oxidase.

DETAILED DESCRIPTION OF THE INVENTION

There is no specific limitation on the water-impermeable, light-transmissive support comprised in the multilayer analytical element of the present invention, so far as it allows transmission of applied electromagnetic waves in the wavelength range of approx. 200 nm to approx. 900 nm, such as ultraviolet rays, near-ultraviolet rays, visible rays and near-infrared rays at a ratio of not less than approx. 40%, preferably not less than approx. 65%, permits substantially no permeation of water thereinto, and is substantially chemically inert to a polymer binder and other materials comprised in the hereinafter-described reagent layers and undercoating layer to be superposed on the support. Examples of the support include a transparent sheet or film made of a polymer such as polyethylene terephthalate, polycarbonate of bisphenol A, polymethyl methacrylate, polystyrene, cellulose esters (e.g., cellulose diacetate, cellulose triacetate, and cellulose acetate propionate) and a transparent glass plate. The thickness of the support generally ranges from approx. 50 μm to approx. 2 mm, preferably from approx. 70 μm to approx. 0.5 mm.

On a surface of the support can be provided a known undercoating layer for facilitating adhesion of a reagent layer or one of other functional layers to the support so as to form an integrated structure. For the same purpose, the surface of the support can be modified by a known chemical processing such as acid processing or alkaline processing, or a known physical processing such as corona discharge processing, glow discharge processing, ultraviolet rays irradiation processing or flame processing.

The reagent layer containing at least a peroxidase which is comprised in the multilayer analytical element of the present invention is a reagent layer which comprises a hydrophilic polymer binder and a color-forming indicator composition for detection of hydrogen peroxide (referred to hereinafter as "color-forming reagent for $H_2O_2$") containing at least a peroxidase, the latter being dispersed or dissolved in the matrix of the former polymer binder.

The color-forming reagent for $H_2O_2$ comprises a peroxidase and an indicator (including one compound or a combination of two or more compounds) which shows a detectable change (generally, change of color density, or change of hue) in the presence of peroxidase and hydrogen peroxide.

Examples of the indicator include the following.

(1) a combination of 4-aminoantipyrine or a derivative thereof (chromogen) and phenol, naphthol, or a derivative thereof (coupler) disclosed in Ann. Clin. Biochem., 6, 24–27(1969), U.S. Pat. Nos. 3,992,158, 3,983,005 and 4,292,272, EP No. 0033539 A2, EP No. 0033540 A2, DE No. 3 301 470 A1, and Japanese Patent Provisional Publication No. 58(1983)-124771.

Examples of the phenol derivative and naphthol derivative include compounds described in The Theory of the Photographic Process, Third Edition, edited by C. E. K. Mees & T. H. James (Macmillan Co., New York, 1966), pp. 387–396.

(2) A combination of a 5-pyrazolone derivative or 4-oxazolone derivative (chromogen) and a phenol or a naphthol (coupler) as disclosed in FR No. (French Patent) 2 185 289.

(3) A combination of a 4-aminopyrazolone derivative such as 1-(4-sulfophenyl)-2-methyl-3-phenyl-4-amino-3-pyrazolin-5-one (chromogen) and phenol, a phenol derivative or a polyvalent phenol such as catechol, resorcinol, hydroquinone, or pyrogallol (coupler) as disclosed in Japanese Patent Provisional Publication No. 49(1974)-114987.

(4) A combination of a (p-toluenesulfonylhydrazino)-benzothiazolium, quinolinium or pyridinium derivative (dye forming compound) and phenol, naphthol, a drivative thereof, an aromatic amine, or a reactive methylene-containing compound as disclosed in U.S. Pat. No. 4,089,747. A triarylimidazole derivative serving per se as a dye precursor disclosed in said Publication is employed even singly.

(5) A combination of 4-aminoantipyrine, a 4-substituted antipyrine, an N,N-di-substituted-o- or p-phenylenediamine, a 2-hydrozonobenzothiazoline or a p-halogenophenol (hydrogen doner, chromogen) and an N,N-di-substituted aniline (coupler) as disclosed in GB No. 2 095 401A and Japanese Patent Provisional Publication No. 57(1982)-142562.

(6) A combination of an o- or p-aminophenol compound or an o- or p-phenylenediamine compound and a non-diffusion (diffusion-resistant) phenol compound, a non-diffusion naphthol compound, a nondiffusion acylacetamide compound or a nondiffusion pyrazolone compound as disclosed in Japanese Patent Provisional Publications No. 57(1982)-94653, No. 57(1982)-94654, No. 57(1982)-94655, and No. 56(1982)-94656.

Among these indicators, the combination of 4-aminoantipyrine or a derivative thereof and naphthol or a derivative thereof is preferred. Particularly preferred are a combination of 4-aminoantipyrine and 1,7-dihydroxynaphthalene as well as a combination of 4-amino-2,3-dimethyl-1-(2,4,6-trichlorophenyl)-3-pyrazolin-5-one and 1,7-dihydroxynaphthalene.

Peroxidase can be a peroxidase of plant or animal origin (EC 1.11.1.7) as disclosed in U.S. Pat. Nos. 3,983,005 and 4,211,845, GB No. 2 036 963A, and others, or a peroxidase of microorganism origin (EC 1.11.1.7) as disclosed in Japanese Patent Provisional Publication No. 57(1982)-99192 and others. The peroxidase can be employed alone or in combination.

Alternatively, inorganic compounds having the peroxidase activity such as ferrous thiocyanate, ferrous tannate, ferrous ferrocyanide, potassium chromic sulfate, sodium iodide, potassium iodide, ammonium molybdate, and potassium molybdate as disclosed in U.S. Pat. Nos. 3,983,005 and 4,211,845 and GB No. 2 036 963A can be employed.

Among these peroxidases and other compounds having the peroxidase activity, peroxidases of plant origin and non-specific peroxidases of microorganism origin are preferred.

As described hereinbefore, the reagent layer containing at least a peroxidase, which is comprised in the multilayer analytical element of the present invention, is a reagent layer which comprises a hydrophilic polymer binder and a color-forming indicator composition (containing a peroxidase) dispersed or dissolved in the binder.

There is no specific limitation on a hydrophilic polymer employable as the polymer binder, so far as the polymer is capable of forming a film and is substantially inert to both the peroxidase and the indicator composition. Examples of the hydrophilic polymer include gelatin, acid-processed gelatin, deionized gelatin, gelatin derivatives such as acylated gelatin, poly(vinyl alcohol), poly(vinylpyrrolidone), poly(sodium vinylbenzenesulfonate), carboxymethyl cellulose, sodium carboxymethylcellulose, hydroxyethylcellulose, methylcellulose, pullulan, pullulan derivatives, polyacrylamide, and acrylamide copolymers such as acrylamide—N-vinylpyrrolidone copolymer and acrylamide—2-hydroxyethylacrylamide copolymer. The thickness (dry basis) of the reagent layer generally ranges from approx. 5 $\mu$m to approx. 100 $\mu$m, preferably from approx. 10 $\mu$m to approx. 50 $\mu$m.

The peroxidase contained in the reagent layer generally amounts to approx. 5,000 U/m$^2$ to approx. 100,000 U/m$^2$, preferably from approx. 10,000 U/m$^2$ to approx. 60,000 U/m$^2$.

The indicator composition is necessarily incorporated in an amount equivalent to or more than the amount stoichiometrically corresponding to the presumed maximum amount of the analyte contained in the liquid sample under analysis. The amount of the indicator composition employed can be determined by those skilled in the art through experimental trials.

There will be given description hereunder on the water-soluble monocarboxylic acid or a salt thereof (referred to herein as simply "water-soluble monocarboxylic acid(s)" or "monocarboxylic acid(s)") having solubility of not less than 1 g. in 100 g. of water at 25° C.

The water-soluble monocarboxylic acid is included in at least one layer other than the support of the multilayer analytical element of the present invention. In the case where the water-soluble monocarboxylic acid is included in a layer comprising a hydrophilic binder polymer, said monocarboxylic acid is preferably dispersed or dissolved in the hydrophilc binder.

As the water-soluble monocarboxylic acids, there can be mentioned an aliphatic monocarboxylic acid or a salt thereof, an aromatic monocarboxylic acid or a salt thereof, and an aromatic group-substituted aliphatic monocarboxylic acid or a salt thereof. These water-soluble monocarboxylic acids can be employed singly or in combination.

The aliphatic monocarboxylic acid can be a straight-chain or branched-chain saturated aliphatic monocarboxylic acid having 1-5 carbon atoms, such as formic acid, acetic acid, propionic acid, butyric acid, valeric acid, isobutyric acid or isovaleric acid. The salt of an aliphatic monocarboxylic acid can be an alkali metal salt of the straight-chain or branched-chain saturated aliphatic monocarboxylic acid having 1-5 carbon atoms, such as a lithium salt, a sodium salt, or a potassium salt. Otherwise, an ammonium salt can be employed. Examples of the salt include a lithium salt, a sodium salt, a potassium salt and an ammonium salt of formic acid, acetic acid, propionic acid, butyric acid, valeric acid, isobutyric acid and isovaleric acid.

Examples of the salt of aromatic monocarboxylic acids include lithium benzoate, sodium benzoate, potassium benzoate, ammonium benzoate, sodium o-toluylate, sodium m-toluylate, sodium p-toluylate, and ammonium o-toluylate.

Examples of the aromatic group-substituted aliphatic monocarboxylic acid include phenylacetic acid, sodium phenylacetate, potassium phenylacetate, and ammonium phenylacetate.

Among these water-soluble monocarboxylic acids, preferred are acetic acid, propionic acid, sodium formate, potassium formate, sodium acetate, potassium acetate, ammonium acetate, sodium propionate, potassium propionate, and ammonium propionate.

The water-soluble monocarboxylic acid is ordinarily employed singly for inclusion in at least one layer of the multilayer analytical element. Otherwise, two or more of the water-soluble monocarboxylic acids can be included in at least one layer, or included individually in two or more layers.

The water-soluble monocarboxylic acid can be in the liquid or solid form. The solid acid can contain one or more crystalline water or alcohol.

The water-soluble monocarboxylic acid can be included in the reagent layer containing peroxidase, or in any other layers (including a porous spreading layer) provided over the reagent layer containing peroxidase, that is, any other layers placed on the side opposite to the support with respect to the peroxidase-containing reagent layer. Otherwise, the water-soluble monocarboxylic acid can be included in both the peroxidase-containing reagent layer and another layer (or other layers) provided thereover or the spreading layer. If the water-soluble monocarboxylic acid disturbs the action of the peroxidase or oxidase employed, said acid can be included in another layer (or other layers) than the layer containing the peroxidase or oxidase, and moreover these two or more layers can be separated by providing an intermediate layer therebetween in a position adjacent to the latter layer. If an analyte or an oxidation product thereof obtained by the action of oxidase is per se the water-soluble monocarboxylic acid (or an ion thereof), or the employed water-soluble monocarboxylic acid intereferes or inhibits specifically a series of the reactions taking place on the analyte within the multilayer analytical element, the water-soluble monocarboxylic acid should be replaced with one of alternative water-soluble monocarboxylic acids.

It will be understood that the necessary amount of the water-soluble monocarboxylic acid introduced into the multilayer analytical element varies depending upon the amount of substances showing the catalase activity, and the catalase activity value, as well as depending upon the amount of the liquid sample applied to the spreading layer of the multilayer analytical element. The amount of the water-soluble monocarboxylic acid to be incorporated into in the multilayer analytical element generally ranges from 0.1 meq. to 1 eq., preferably from 0.2 meq. to 0.5 eq. based on 1 $m^2$ of the multilayer analytical element.

If the analyte per se is not hydrogen peroxide, but is able to produce hydrogen peroxide by a chemical reaction, an oxidase serving as a catalyst for the reaction between the analyte and oxygen for producing hydrogen peroxide can be included in the reagent layer or other layers. The oxidase included in the multilayer analytical element is chosen according to nature of the analyte. The oxidase can be employed singly, but a plurality of enzymes (containing at least one oxidase) can be employed for causing a series of continuous reactions. If required, a cofactor or an activator to the oxidase and/or its coenzyme can be employed in conjunction with the oxidase.

The oxidase, together with a coenzyme thereof if required, can be included in a reagent layer containing peroxidase and a combination of a chromogen and a coupler or in a layer provided over the reagent layer. Otherwise, it can be included in the reagent layer containing peroxidase and a combination of a chromogen and a coupler, as well as in one or more layers provided over the reagent layer. Thus, it can be included in two or more layers. The above-mentioned term "a layer provided over the reagent layer" means to include a porous spreading layer.

A reaction of a substrate catalyzed by an oxidase requires oxygen. In this respect, since oxygen in a circumferential air is to be introduced from a porous spreading layer to diffuse into other layers, a multilayer analytical element in which the oxidase is included in a layer provided over the reagent layer containing peroxidase and a combination of a chromogen and a coupler, particularly in a porous spreading layer or a layar adjacent to the spreading layer so as to accomplish efficient diffusion of oxygen into the layers, which is disclosed in GB No. 2 104 215A, is preferably employed for facilitating efficient progress of the oxidation reaction catalyzed by the oxidase. In the case where the analyte is a hydrophobic substance such as a cholesterol ester, the analyte difficultly permeates the layer having a hydrophilic polymer binder. For this reason, the oxidase is preferably included inside of the porous spreading layer in such a case.

The oxidase contained in the multilayer analytical element of the present invention may be an oxidase utilizing oxygen ($O_2$) as acceptor. Examples of the oxidase utilizing oxygen ($O_2$) as acceptor include the following enzymes: the number included in parenthesis given to the listed enzyme meaning EC number: glucose oxidase (1.1.3.4), hexose oxidase (1.1.3.5), cholesterol oxidase (1.1.3.6), galactose oxidase (1.1.3.9), alcohol oxidase (1.1.3.13), pyruvate oxidase (1.2.3.3), uricase (ureate oxidase) (1.7.3.3), lactate oxidase (lactate 2-monooxygenase) (1.13.12.4), glycerol oxidase (available from Toyo Jozo Co., Ltd., Japan), ascorbate oxidase (1.10.3.3) and L-α-glycerophosphate oxidase (1.1.99.5).

Examples of the combination of a plurality of enzymes including oxidase include those described in FR No. 2 362 396, U.S. Pat. No. 3,983,005, and DE No. 3 222 707 A1.

The amount of the oxidase to be incorporated into the multilayer analytical element can be determined principally by the ratio between the presumed maximum amount of the hydrogen peroxide-producible analyte contained in a liquid sample under analysis and activity values of the oxidase and peroxidase. Thus, the amount of the oxidase can be determined experimentally by those skilled in the art. The amount of the oxidase generally ranges from approx. 1,000 $U/m^2$ to approx. 100,000 $U/m^2$, and preferably ranges from approx. 3,000 $U/m^2$ to approx. 50,000 $U/m^2$. In the case that oxidase is glucose oxidase, the amount generally ranges from approx. 2,000 $U/m^2$ to approx. 40,000 $U/m^2$, and preferably ranges from approx. 4,000 $U/m^2$ to approx. 20,000 $U/m^2$.

Each of the peroxidase and oxidase has an optimum pH range respectively where its activity is kept at the maximum value. Said activies are also influenced by an ionic strength and natures of anions and cations present in the vicinity of these enzymes. Accordingly, it is very important for obtaining results satisfactory in the quantitative accuracy, reproducibility, etc. that the multilayer analytical element is so prepared that primarily a pH value of a reagent layer containing peroxidase, a reagent layer containing oxidase (or a reagent layer containing both peroxidase and oxidase) is adjusted to a respective optimum value, and that, if necessary, other factors such as the ionic strength and nature of coexisting ions are adjusted to show optimum conditions.

In order to produce a detectable change in the presence of hydrogen peroxide in the reagent layer containing peroxidase and a combination of a chromogen and a coupler, the pH value is preferably adjusted to the range of pH 5.0 (approx.) to pH 9.0 (approx.), preferably pH 6.0 (approx.) to pH 8.0 (approx.).

The layer containing oxidase is preferably adjusted to have an optimum pH value or a pH value in the vicinity of the optimum value, according to the requirment of nature of the oxidase contained therein.

Different oxidases have their own optimum pH values: for instance, pH 5.6 (approx.) for glucose oxidase; pH 6.3 (approx.) for hexose oxidase; pH 5.8 (approx.) for cholesterol oxidase; pH 7.0 (approx.) for galactose oxidase; pH 7.5 (approx.) for alcohol oxidase; pH 7.5-8.5 for uricase; pH 5.6 (approx.) for ascorbate oxidase; and pH 7.5-7.7 for L-α-glycerophosphate oxidase.

An oxidase having an optimum pH value different from an optimum pH value of a peroxidase employed together is preferably included in a layer different from the peroxidase-containing layer. For instance, glucose oxidase can be included in a porous spreading layer or an adhesive layer (which will be described hereinafter). In this case, said layer containing glucose oxidase can be so prepared to show under analytical conditions pH 5.6 of the optimum pH value for glucose oxidase or a value in the vicinity of pH 5.6, such as, in the range of pH 4.0 to pH 7.0, by incorporating an acid or a buffer thereinto.

Examples of the acid, alikali and buffer reagent employable for adjusting the pH conditions of the reagent layer, other layers or the porous spreading layer include malic acid, tartaric acid, citric acid, 3,3-dimethylglutaric acid, acetic acid, propionic acid, butyric acid, sodium hydroxide, potassium hydroxide, potassium hydrogen citrate - citric acid, potassium dihydrogenphosphate-potassium hydrogenphosphate, and buffer reagents described in "Hydrogen Buffers for Biological Research" reported by Norman E. Goods, et al.: Biochemistry, 5(2), 467–477 (1966), "Data for Biochemical Research" Vol. 2 (Oxford at the Clarendon Press, 1966) pp. 476–508, Analytical Biochemistry, 104, 300–310 (1980), etc., (examples: 2-(N-morpholino)ethanesulfonic acid, sodium salt or potassium salt of N-2-hydroxyethyl-piperazine-N'-2-hydroxypropane-3-sulfonic acid (Heppso), sodium salt or potassium salt of N-2-hydroxyethylpiperazine-N'-3-propanesulfonic acid (Epps), etc.), other buffer reagents (examples: sodium or potassium hydrogenmalate, sodium or potassium monohydrogen-3,3-dimethylglutarate, etc.), and inorganic acids (examples: sulfuric acid, phosphoric acid, etc.).

The multilayer analytical element of the present invention may contain a compound comprising a cation capable of forming in combination with $F^-$ ion a sparingly water-soluble salt having solubility of not more than 0.2 g. in 100 g. of water at 25° C. (referred to herein as "sparingly soluble F salt-forming compound") in one or more layers selected from the group consisting of the reagent layer, other layers provided over the reagent layer, or the porous spreading layer, whereby eliminating interferences, namely, reduction or fluctuation of a measured value caused by NaF contained as preservative in a whole blood, a plasma, and a serum. The arts relating to incorporation of the sparingly soluble F salt-forming compound is disclosed in our U.S. patent application Ser. No. 517,341 filed on July 26, 1983 incorporated herein by reference and EPC application (No. 83107440.6). The above-mentioned cation can be $Mg^{2+}$, $Ca^{2+}$, and $Ba^{2+}$. The sparingly soluble F salt-forming is generally introduced into the multilayer analytical element of the invention in an amount ranging from 0.1 meq. to 1 eq., preferably from 0.2 meq. to 0.5 eq. based on 1 $m^2$ of the multilayer analytical element.

The porous spreading layer (referred to herein as "spreading layer") of the multilayer analytical element of the present invention is arranged in the outmost position of the element. In other words, the spreading layer is provided in the outmost position far from the support via the reagent layer. The liquid sample is applied or spotted onto the spreading layer. The function of this layer is to supply a liquid sample together with an analyte contained therein into the reagent layer at an approximately constant volume per unit area regardless of its applied volume, that is to say, "metering effect". Thus, this layer acts as a spreader for a liquid sample. Because of such spreading action, a volume of the liquid sample supplied to the reagent layer per unit area is automatically adjusted to a certain value regardless of its applied volume. This means that a liquid sample can be analyzed quantitatively without precise measurement of the volume when applied to the multilayer analytical element. However, it should be understood that the use of the multilayer analytical element of the invention never excludes making precise measurement of a liquid sample in carrying out a quantitative analysis procedure. The precise measurement of a liquid sample is sometimes advantageous to increase accuracy of the analysis.

Example of the porous spreading layer of the present invention include non-fibrous, an isotropically porous layer as disclosed in Japanese Patent Provisional Publication No. 49(1974)-53888, U.S. Pat. No. 3,992,158, and GB No. 1 440 464; an isotropically porous layer being formed by three-dimensional matrix in which fine spherical beads are bound in point-to-point contact in all directions, as disclosed in U.S. Pat. No. 4,258,001; a fibrous, anisotropically porous spreading layer consisting of water-washed fabrics or hydrophilically processed fabrics, as disclosed in U.S. Pat. No. 4,292,272; a fibrous, anisotropocally porous spreading layer consisting of fabrics having phisically activated surfaces, as disclosed in GB No. 2 087 074A; and a fibrous, anisotropic porous spreading layer consisting of paper, paper filter or no-woven fabrics containing synthetic polymer fiber pulps, as disclosed in GB No. 2 087 074A. Any of these spreading layers can be provided to the analytical element of the invention in such manners as those disclosed in these patent specifications. Otherwise, the spreading layer also serving as a light-shielding layer (radiation-blocking layer, white background layer, or light-reflecting layer) disclosed in U.S. Pat. No. 3,992,158 and GB No. 1 440 464, can be employed in the analytical element of the invention, details being given hereinafter. If a liquid sample is a whole blood, the spreading layer preferably is the aforementioned isotropically porous layer having continuous voids and being formed by three-dimensional matrix, or the fibrous, anisotropically porous spreading layer.

The multilayer analytical element of the invention can be provided with a light-shielding layer capable of allowing permeation of water and analyte, between the reagent layer and the spreading layer.

The light-shielding layer is advantageously provided if the analytical element is employed for analysis of a liquid sample containing colored particles such as the whole blood containing red corpuscles. In more detail, colored particles positioned on one side of the light-shielding layer are photometrically shielded by the light-shielding layer from observation through the transparent support. Accordingly, the colorimetric or fluorometric measurement is not interfered by the presence of the colored particles. The light-shielding layer can be composed of a fine powder such as finely particulated titanium dioxide, barium sulfate, or zinc oxide dispersed within a hydrophilic polymer binder. The light-shielding layer has a thickness in the range of from 5 to 100 μm, preferably 5 to 30 μm. The binder for the preparation of the light-shielding layer can be optionally selected from the hydrophilic polymers described hereinbefore in connection with the binder for the reagent layer.

The multilayer analytical element of the present invention can be provided with an adhesive layer for superposing the spreading layer on the reagent layer, the light-shielding layer, or other optionally-placed layers under increased adhesion to form an integrally laminated structure.

The multilayer analytical element of the invention can be provided, if desired, with a variety of layers such as a barrier layer or a liquid-blocking layer disclosed in U.S. Pat. No. (Re) 30,267, Japanese Patent Provisional Publication No. 58(1983)-77660 and GB No. 2 114 737A, etc.; a detection layer or a mordant layer disclsoed in U.S. Pat. Nos. 4,042,335 and 4,144,306, etc.; a migration inhibiting layer disclosed in U.S. Pat. No. 4,166,093; the intermediate layer disclosed in U.S. Pat. Nos. 4,098,574 and 4,042,335, etc.; a protein-permeable hydrophilic polymer binder layer disclosed in U.S. Pat. Nos. 4,144,306 and 4,268,563, GB No. 1 474 285, EP No. 0044775 A1, U.S. Pat. No. 4,333,733, Japanese Patent Application No. 57(1982)-61936, etc.; a reagent layer comprising hydrophobic particles in which a reagent is contained under dispersion in a hydrophilic binder disclosed in U.S. Pat. No. 4,356,149; a porous material (patch) for application and supply of a liquid sample in a certain limited area disclosed in DE No. 3 133 538 A1; and a porous layer having a certain limited area and containing a reagent such as enzyme disclosed in DE No. 3 222 707 A1.

The multilayer analytical element of the present invention comprises, in sequence, a spreading layer, a reagent layer containing peroxidase, and a transparent support.

Among arrangements of the various layers, preferred are:

an arrangement comprising, in sequence, a spreading layer, a light-shielding layer, a reagent layer containing peroxidase, and a transparent support;

an arrangement comprising, in sequence, a spreading layer, an adhesive layer, a light-shielding layer, a reagent layer containing peroxidase, and a transparent support;

an arrangement comprising, in sequence, a spreading layer, a light-shielding layer containing oxidase, a reagent layer containing peroxidase, and a transparent support;

an arrangement comprising, in sequence, a spreading layer, an adhesive layer containing oxidase, a light-shielding layer, a reagent layer containing peroxidase, and a transparent support;

an arrangement comprising, in sequence, a spreading layer containing oxidase, an adhesive layer containing oxidase, a light-shielding layer, a reagent layer containing peroxidase, and a transparent support;

an arrangement comprising, in sequence, a spreading layer, an adhesive layer containing oxidase, a light-shielding layer containing oxidase, a reagent layer containing peroxidase, and a transparent support;

an arrangement comprising, in sequence, a spreading layer, a light-shielding layer, a reagent layer containing both peroxidase and oxidase, and a transparent support;

an arrangement comprising, in sequence, a spreading layer, an adhesive layer, a light-shielding layer containing oxidase, a reagent layer containing both peroxidase and oxidase, and a transparent support;

an arrangement comprising, in sequence, a spreading layer, a reagent layer containing oxidase, a light-shielding layer, a reagent layer containing both peroxidase and oxidase, and a transparent support; and other variations of the above-described arrangements.

The multilayer analytical element of the present invention can be prepared in the manners disclosed in the aforementioned patent specifications. Examples of the detailed procedures are described in the hereinafter-given working examples.

The multilayer analytical element of the present invention can be employed in quantitative analysis of analytes contained in a variety of liquid samples in the same manners as disclosed in the aforementioned patent specifications. The analytical element of the invention is preferably received in a slide frame and employed in the form of an analytical slide as disclosed in Japanese Utility Model Provisional Publication No. 54(1979)-162294, U.S. Pat. Nos. 4,387,990 and 4,169,751, and Japanese Patent Provisional Publication No. 57(1982)-63452. Otherwise, the analytical element of the invention is preferably provided with a liquid sample-spreading assistant material (or a sample-spreading assisting element) on the porous spreading layer to form an analytical slide as disclosed in Japanese Patent Provisional Publication No. 57(1982)-182648. The analytical element in the form of such a slide is preferred in all aspects, namely, preparation, transportation, storage, measurement procedure and so forth.

The present invention will be further described by the following examples, which are not given to restrict the invention.

EXAMPLE 1

A reagent layer for quantitative analysis of glucose concentration in blood, having a thickness of 15 $\mu m$ (dry basis) was formed on a transparent polyethylene terephthalate (PET) film (thickness: 185 $\mu m$) having a gelatin subbing layer, by coating the following composition thereon.

| | |
|---|---|
| Peroxidase | 25000 IU |
| 1,7-Dihydroxynaphthalene | 5 g. |
| 4-Aminoantipyrine | 5 g. |
| Gelatin | 200 g. |
| Nonion HS 210 (polyoxyethylene-nonylphenyl ether: produced by Nippon Oils & Fats Co., Ltd., Japan) | 2 g. |

On the reagent layer, a light-shielding layer having a thickness of 15 $\mu m$ (dry basis) was formed by coating thereon an aqueous coating solution which contained 8 g. of powdery titanium dioxide having 0.2 g. of Nonion HS 210 and 50,000 IU of glucose oxidase and 1 g. of gelatin dispersed in water.

On the light-shielding layer, an adhesive layer having a thickness of 4 $\mu m$ (dry basis) was formed by coating thereon an aqueous coating solution containing 4 g. of gelatin, 2 g. of sodium acetate, and 0.2 g. of Nonion HS 210 in 100 ml. of water.

The adhesive layer was wetted with water in an amount of 30 g./m$^2$, and subsequently a cotton broadcloth (100% cotton, woven from cotton yarn of 100 count, manufactured by Toyobo Co., Ltd., Japan) was pressed onto the adhesive layer and dried to give a porous spreading layer. Thus, a multilayer analytical element for quantitative analysis of glucose was prepared.

The analytical element was cut to obtain a square tip (1.5 cm×1.5 cm), which was in turn inserted into a plastic mount disclosed in U.S. patent application Ser. No. 308,205, filed Oct. 2,1981 (Japanese Patent Provisional Publication No. 57(1982)-63452), to prepare an analytical slide for quantitative analysis of glucose.

The liquid sample for analysis was prepared by adding different amounts of glucose to a human plasma which was obtained by collecting a blood in the presence of heparin and then subjecting the blood to centrifugal separation. The liquid sample in the amount of 10 $\mu l$. was spotted on the spreading layer of the analytical slide, which was then incubated at 37° C. for 6 min., and subjected to reflective spectroscopy at 500 nm. The results are set forth in Table 1.

COMPARISON EXAMPLE 1

A control analytical slide was prepared in the same manner as in Example 1 except for incorporating no sodium acetate into the adhesive layer.

The analytical slide was then incubated and subjected to reflective spectroscopy in the same manner as in Example 1. The results are set forth in Table 1.

TABLE 1

(Glucose Content in Human Plasma and Optical Density of Formed Color)

| Analytical Element | Glucose Content (mg./dl.) | | | | | |
|---|---|---|---|---|---|---|
| | 0 | 100 | 200 | 300 | 500 | 600 |
| Example 1 | 0.19 | 0.61 | 0.85 | 1.11 | 1.47 | 1.60 |
| Comparison Example 1 | 0.19 | 0.50 | 0.72 | 0.95 | 1.32 | 1.43 |

The results in Table 1 clearly indicate that the multilayer analytical element of the invention showed increase of the optical density of the formed color, in comparison with the comparison example.

EXAMPLE 2

A human whole blood was collected in the presence of heparin and NaF and then subjected to centrifugal separation to obtain a plasma. Determination by the glucose oxidase enzyme-electrode method indicated that the plasma contained 108 mg./dl of glucose.

A portion of the above plasma was partially hemolyzed to obtain a partially hemolytic plasma containing 137 mg./dl of hemoglobin.

Analytical slides for quantitative analysis of glucose were prepared in the same manner as in Example 1 and Comparison Example 1.

One of the above-mentioned two plasmas was spotted on the spreading layer of the analytical slide in the same manner as in Example 1. The analytical slide was then incubated and subjected to reflective spectroscopy in the same manner as in Example 1. The results are set forth in Table 2.

TABLE 2

(Optical Density of Formed Color in the Analysis on Plasma and Partially Hemolytic Plasma)

| Analytical Element | Plasma | Partially Hemolytic Plasma |
|---|---|---|
| Element of Example 1 (According to the invention) | 0.63 | 0.62 |
| Element of Comparison Example 1 (Control) | 0.60 | 0.54 |

It was confirmed that a chemical analytical slide using the multilayer analytical element of the present invention is highly prevented from the interference arising from hymolytic hemoglobin and increased in the optical density of formed color.

EXAMPLES 3 & 4

Analytical slides for quantitative analysis of glucose were prepared in the same manner as in Example 1 except for replacing sodium acetate with 1.5 g. of acetic acid (Example 3) and ammonium acetate (Example 4).

A human whole blood was collected in the presence of heparin and NaF and then subjected to centrifugal separation to obtain a non-hemolytic plasma (liquid sample). Determination by the glucose oxidase enzyme-electrode method indicated that the non-hemolytic plasma contained 200 mg./dl of glucose.

The liquid sample in the amount of 10 μl. was spotted on the spreading layer of the analytical slide, which was then incubated at 37° C. for 6 min., and subjected to reflective spectroscopy at 500 nm. The results are set forth in Table 3.

EXAMPLE 5

An analytical slide for quantitative analysis of glucose was prepared in the same manner as in Example 1 except for replacing sodium acetate with 1.0 g of sodium formate.

The analytical slide was then subjected to the color formation test in the same manner as in Example 3. The results are set forth in Table 3.

EXAMPLE 6

An analytical slide for quantitative analysis of glucose was prepared in the same manner as in Example 1 except for replacing sodium acetate with 1.0 g of potassium propionate.

The analytical slide was then subjected to the color formation test in the same manner as in Example 3. The results are set forth in Table 3.

COMPARISON EXAMPLES 2-6

Analytical slides for quantitative analysis of glucose were prepared in the same manner as in Example 1 except for replacing sodium acetate with 1.0 g of 3,3-dimethylglutaric acid (3,3-DMG, Com. Example 2), tartaric acid (Com. Example 3), sodium citrate (Com. Example 4), disodium monohydrogenphosphate ($Na_2HPO_4$, Com. Example 5), and monopotassium dihydrogenphosphate ($KH_2PO_4$, Com. Example 6). Further, a control analytical slide was prepared in the same manner as in Comparison Example 1.

The analytical slide was then subjected to the color formation test in the same manner as in Example 3. The results are set forth in Table 3.

TABLE 3

(Influence of Various Acid and Salt)

| Analytical Element | Acid or Salt Incorporated | Optical Density of Formed Color |
|---|---|---|
| Example 3 | Acetic acid | 0.77 |
| Example 4 | Ammonium acetate | 0.79 |
| Example 5 | Sodium formate | 0.78 |
| Example 6 | Sodium propionate | 0.76 |
| Com. Ex. 1 | Not incorporated | 0.73 |
| Com. Ex. 2 | 3,3-DMG | 0.72 |
| Com. Ex. 3 | Tartaric acid | 0.73 |
| Com. Ex. 4 | Sodium citrate | 0.72 |
| Com. Ex. 5 | $Na_2HPO_4$ | 0.71 |
| Com. Ex. 6 | $KH_2PO_4$ | 0.71 |

The results in Table 3 clearly indicate that the multilayer analytical elements of the invention showed increase of the optical density of the formed color.

EXAMPLE 7

An analytical slide for quantitative analysis of glucose was prepared in the same manner as in Example 1 except for employing a spreading layer pre-treated with 10% aqueous sodium acetate solution so as to contain 2 g./m² of sodium acetate in place of the incorporation of sodium acetate into the adhesive layer.

A fresh rabbit whole blood was collected in the presence of heparin and NaF to obtain a liquid sample. The liquid sample in the amount of 10 μl. was spotted on the spreading layer of the analytical slide, which was then incubated and subjected to reflective spectroscopy on the formed color to give optical density of 0.51.

In contrast, the optical density on the color formed on an analytical slide prepared in the same manner as in Comparison Example 1 was 0.46.

EXAMPLE 8

An analytical slide for quantitative analysis of glucose was prepared in the same manner as in Example 1 except for incorporating sodium acetate into the reagent layer (sodium acetate content: 2 g./m$^2$) in place of the adhesive layer.

The analytical slide was then subjected to the color formation test in the same manner as in Example 2, using the non-hemolytic human serum and the partially hemolytic serum. The result indicated that the influence of hemolysis was reduced in this analytical slide.

EXAMPLE 9

An analytical slide for quantitative analysis of glucose was prepared in the same manner as in Example 1 except for incorporating sodium acetate into the light-shielding layer in place of the adhesive layer. Further, an analytical slide containing no sodium acetate was prepared in the same manner as in Comparative Example 1.

The analytical slide was then subjected to the color formation test, using a non-hemolytic rabbit plasma obtained by centrifugal separation of a just collected rabbit whole blood in the presence of heparin. The optical density of the formed color was 0.57.

In contrast, the optical density on the color formed on an analytical slide containing no sodium acetate was 0.54.

EXAMPLE 10

An analytical slide for quantitative analysis of cholesterol was prepared in the same manner as in Example 1 except for replacing glucose oxidase in the aqueous solution for the light-shielding layer with 50,000 IU of cholesterol oxidase and incorporating 25,000 IU of cholesterol esterase into the aqueous coating solution for the adhesive layer.

The analytical slide was subjected to the color formation test described in Example 2, using the non-hemolytic human serum and the partially hemolytic human serum containing free cholesterol and ester-type cholesterol in the amount of 375 mg./dl. (calculated in terms of free cholesterol amount). The color formed upon incubation at 37° C. for 6 min. was measured by reflective spectroscopy at 500 nm. The optical densities were 0.47 and 0.45, respectively.

COMPARISON EXAMPLE 7

An analytical slide was prepared in the same manner as in Example 10 except for using no sodium acetate, and subjected to the color formation test described in Example 10 using the same sample as in Example 10. The color formed upon incubation at 37° C. for 6 min. was measured by reflective spectroscopy at 500 nm. The optical densities were 0.44 for the non-hymolytic serum and 0.41 for the hemolytic serum.

EXAMPLE 11

The pH values under analytical conditions (reaction conditions) were measured on the slides prepared in Example 1 and Comparison Example 1 thourgh the experiments described below, in which the pH measurement was carried out by means of a pH meter HM 15 (manufactured by Toa Denpa Co., Ltd., Japan) connected with an electrode for surface pH measurement (GS-165F).

On the analytical slide for quantitative analysis of glucose was spotted 10 μl. of one of three liquid samples, namely, distilled water deionized by ion-exchange (pH 7.0), a control serum (pH 8.4), and a fresh human plasma (pH 7.4). Upon the liquid sample was spread in the element, the porous spreading layer was removed from the element. Subsequently, the pH electrode was brought into contact with the free surface of the adhesive layer of the element, and pH value was measured after the lapse of 6 min. (calculated starting from the time of removal of the spreading layer). The three liquid samples were individually dropped onto a PET film, and the pH values of these drops were measured through the electrode placed in contact with these liquid sample drops. The electrode was calibrated by placing it in close contact with 10 μl. of standard aqueous phosphate solutions of pH 4.01 and 6.86 (25° C.) spotted on the PET film. The results of pH measurements are set forth in Table 4.

The results set forth in Table 4 clearly indicate that the pH value reached an equilibrium value within 2-3 min. for respective case.

Separately, multilayer analytical elments were prepared in the same manner as in Example 1 and Comparative Example 1. From the prepared analytical element, the spreading layer was removed, and then the support was removed therefrom. On the adhesive layer of thus treated element was spotted the liquid sample, and the pH measurements were carried out both on the adhesive layer side and the reagent layer side by means of the electrode (GS-165F) placed in contact with the respective layer. The pH value reached the above-mentioned equilibrium value with ±0.1.

EXAMPLE 12

An analytical slide for quantitative analysis of glucose was prepared in the same manner as in Example 1.

The pH value of the layer under progress of reaction under the analytical conditions was determined using a pH indicator. The pH indicator employed was a masking indicator prepared by mixing Bromothimol Blue (BTB) and Bromothimol Purple (BTP). A calibration curve indicating the relationship between the color formation of the indicator and the pH value was in advance prepared by calibrating the indicator in a phosphate buffer by the use of a buffer solution having a known pH value (this pH value was calibrated by means of a pH meter) and then obtaining the absorption spectrum thereon by means of Hitachi 340 spectrophotometer.

On the porous spreading layer of the analytical slide for glucose was spotted one of three liquid samples, namely, distilled water deionized by ion-exchange (pH 7.0), a control serum (pH 8.4), and a fresh human plasma (pH 7.4) after incorporation of a small amount of the above-mentioned masking indicator into each liquid sample. After the lapse of 5 min., the color formation of the masking indicator was measured from the PET film (support) side. Since the detectable color formation given in the case of the control serum and the plasma overlapped in the wavelength with the color formation of glucose, the reflective spectroscopic measurement was carried out through the dual wavelength method by means of the Hitachi 340 spectrophotometer so as to eliminate the influence of color formation stemmed from the glucose. The results are set forth in Table 4.

TABLE 4

|  | Distilled & Ion-exchanged Water (pH 7.0) | Fresh human Plasma (pH 7.4) | Control Serum (pH 8.4) |
| --- | --- | --- | --- |
| Example 11 Measurement from adhesive layer side |  |  |  |
| Sodium acetate-containing slide | 6.1 | 6.2 | — |
| No sodium acetate-containing slide | 5.9 | 6.0 | — |
| Measurement on PET film | 7.0 | 7.4 | — |
| Example 12 Measurement from PET film side |  |  |  |
| Sodium acetate-containing slide | 6.5 | 6.8 | 6.7 |

Remark: In Example 11, the experiment on the control serum was not carried out.

Comparison between the pH values and the results given in Examples 1 through 9 and Comparison Examples 1 through 6 indicates that the multilayer analytical element containing a water-soluble monocarboxylic acid or a salt thereof according to the present invention showed increase of the optical density of the formed color regardless of variation of pH values under reaction, thus indicating effective prevention on interference arising from the catalase activity.

We claim:

1. In a multilayer analytical element comprising a water-impermeable, light-transmissive support, a reagent layer containing at least a peroxidase, and a porous spreading layer, which are superposed in this order, the improvement which comprises at least one layer other than said support containing a water-soluble monocarboxylic acid or a salt thereof having solubility of not less than 1 g. in 100 g. of water at 25° C.

2. The multilayer analytical element as claimed in claim 1, in which said monocarboxylic acid is an aliphatic monocarboxylic acid or an aromatic monocarboxylic acid.

3. The multilayer analytical element as claimed in claim 1, in which said monocarboxylic acid or salt thereof is at least one compound selected from the group consisting of formic acid, acetic acid, propionic acid, butyric acid, valeric acid, benzoic acid, an alkali metal salt thereof, and an ammonium salt thereof.

4. The multilayer analytical element as claimed in claim 3, in which said alkali metal salt is selected from the group consisting of a lithium salt, a potassium salt and a sodium salt.

5. The multilayer analytical element as claimed in any one of claims 1, in which said reagent layer contains 4-aminoantipyrine or a derivative thereof in addition to the peroxidase.

6. The multilayer analytical element as claimed in any one of claims 1, in which an oxidase is contained in said reagent layer or any other layer.

7. The multilayer analytical element as claimed in claims 1, in which said oxidase is selected from the group consisting of glycollate oxidase, malate oxidase, glucose oxidase, hexose oxidase, cholesterol oxidase, L-gulonolactone oxidase, galactose oxidase, xanthine oxidase, pyruvate oxidase, uricase, ascorbate oxidase, lactate oxidase, glycine oxidase, and glycerol oxidase.

8. The multilayer analytical element as claimed in claim 6, in which said oxidase is glucose oxidase.

9. The multilayer analytical element as claimed in claim 6, in which said oxidase is cholesterol oxidase.

* * * * *